United States Patent [19]

Reiner

[11] 4,412,070
[45] Oct. 25, 1983

[54] CEPHALOSPORIN DERIVATIVES

[75] Inventor: Roland Reiner, Basel, Switzerland

[73] Assignee: Hoffmann-La Roche Inc., Nutley, N.J.

[21] Appl. No.: 306,053

[22] Filed: Sep. 28, 1981

[30] Foreign Application Priority Data

Oct. 6, 1980 [CH] Switzerland ............ 7450/80

[51] Int. Cl.³ .......................... C07D 501/56
[52] U.S. Cl. ........................ 544/27; 544/26; 544/182
[58] Field of Search .................. 544/23, 27

[56] References Cited

U.S. PATENT DOCUMENTS 4,200,745 4/1980 Katner ................ 544/21
4,278,793 7/1981 Durckheimer et al. ....... 544/21
4,327,210 4/1982 Mantavon et al. .......... 424/246

Primary Examiner—Paul M. Coughlan, Jr.
Attorney, Agent, or Firm—Jon S. Saxe; Bernard S. Leon; Frank P. Hoffman

[57] ABSTRACT

There is presented compounds of the formula

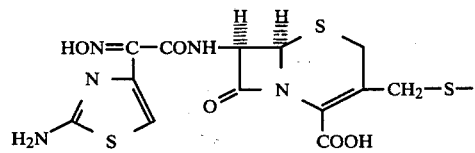

wherein X represents the 1,2,5,6-tetrahydro-2-methyl-5,6-dioxo-as-triazin-3-yl group or its corresponding tautomeric form, the 2,5-dihydro-6-hydroxy-2-methyl-5-oxo-as-triazin-3-yl group, and the readily hydrolyzable esters, readily hydrolyzable ethers and salts of the compounds and hydrates of the compounds of formula I or of their esters, ethers and salts. Also provided is a method of their manufacture and intermediates therefor as well as corresponding pharmaceutical preparations.

8 Claims, No Drawings

CEPHALOSPORIN DERIVATIVES

DESCRIPTION OF THE INVENTION

The present invention relates to novel acyl derivatives, namely cephalosporin derivatives of the formula

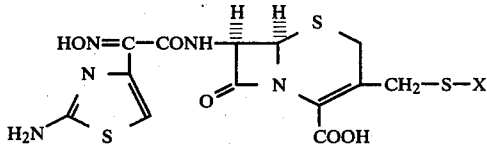   I in which X represents the 1,2,5,6-tetrahydro-2-methyl-5,6-dioxo-as-triazin-3-yl group or its corresponding tautomeric form, the 2,5-dihydro-6-hydroxy-2-methyl-5-oxo-as-triazin-3-yl group, as well as readily hydrolyzable esters, readily hydrolizable ethers and salts of these compounds and hydrates of the compounds of formula I or of their esters, ethers and salts.

As readily hydrolyzable esters of the compounds of formula I there are to be understood compounds of formula I in which the carboxy group is present in the form of a readily hydrolyzable ester group. Examples of such esters, which can be of the conventional type, are the lower alkanoyloxyalkyl esters (e.g. the acetoxymethyl, pivaloyloxymethyl, 1-acetoxyethyl and 1-pivaloyloxyethyl ester), the lower alkoxycarbonyloxyalkyl esters (e.g. the methoxycarbonyloxymethyl, 1-ethoxycarbonyloxyethyl and 1-isopropoxycarbonyloxyethyl ester), the lactonyl esters (e.g. the phthalidyl and thiophthalidyl ester), the lower alkoxymethyl esters (e.g. the methoxymethyl ester) and the lower alkanoylaminomethyl esters (e.g. the acetamidomethyl ester). Other esters (e.g. the benzyl and cyanomethyl esters) can also be used.

As readily hydrolyzable ethers of the compounds of formula I there are to be understood compounds of formula I wherein X signifies the 2,5-dihydro-6-hydroxy-2-methyl-5-oxo-as-triazin-3-yl group in which the enolic OH group is present in the form of a readily hydrolyzable ether group. Possible ether groups are the same groups which have already been mentioned earlier in connection with the readily hydrolyzable ester groups. Examples of such ethers are the lower alkanoyloxyalkyl ethers (e.g. the acetoxymethyl, pivaloyloxymethyl, 1-acetoxyethyl and 1-pivaloyloxyethyl ether), the lower alkoxycarbonyloxyalkyl ethers (e.g. the methoxycarbonyloxymethyl, 1-ethoxycarbonyloxyethyl and 1-isopropoxycarbonyloxy-ethyl ether), the lactonyl ethers (e.g. the phthalidyl and thiophthalidyl ether), the lower alkoxymethyl ethers (e.g. the methoxymethyl ether) and the lower alkanoylaminomethyl ethers (e.g. the acetamidomethyl ether).

Examples of salts of the compounds of formula I are alkali metal salts such as the sodium and potassium salt, the ammonium salt, alkaline earth metal salts such as the calcium salt, salts with organic bases, such as salts with amines (e.g. salts with N-ethyl-piperidine, procaine, dibenzylamine, N,N'-dibenzylethylenediamine, alkylamines or dialkylamines) and salts with amino acids (e.g. salts with arginine or lysine). The salts can be mono-salts or di-salts. The second salt formation can occur in compounds with the hydroxy moiety of the 2,5-dihydro-6-hydroxy-2-methyl-5-oxo-as-triazin-3-yl group.

The compounds of formula I also form addition salts with organic or inorganic acids. Examples of such salts are hydrohalides (e.g. hydrochlorides, hydrobromides and hydroiodides), other mineral acid salts such as sulphates, nitrates, phosphates and the like, alkylsulphonates and monoarylsulphonates such as ethanesulphonates, toluenesulphonates, benzenesulphonates and the like and other organic acid salts such as acetates, tartrates, maleates, citrates, benzoates, salicylates, ascorbates and the like.

The compounds of formula I and their salts, readily hydrolyzable esters and readily hydrolyzable ethers can be hydrated. The hydration can be effected in the course of the manufacturing process or can occur gradually as a result of the hygroscopic properties of an initially anhydrous product.

The products in accordance with the invention can be present in the syn-isomeric form

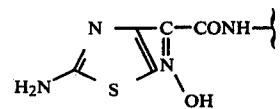

or in the anti-isomeric form

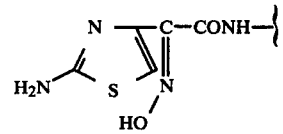

or as a mixture of these two forms. The syn-isomeric form is preferred as are mixtures in which the syn-isomeric form predominates.

Preferred products are:
(6R,7R)-7-[2-(2-amino-4-thiazolyl)-2-(Z-hydroxyimino)acetamido]-3-/[(2,5-dihydro-6-hydroxy-2-methyl-5-oxo-as-triazin-3-yl)thio]-methyl/-8-oxo-5-thia-1-azabicyclo[4.2.0]oct-2-ene-2-carboxylic acid and its salts as well as the corresponding hydrates.

The above acyl derivatives are manufactured in accordance with the invention by (a) reacting a compound of the general formula

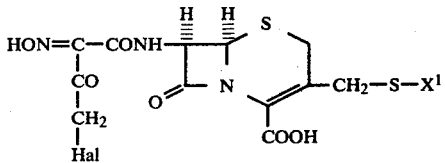   II in which $X^1$ has the same significance as X, whereby the 2,5-dihydro-6-hydroxy-2-methyl-5-oxo-as-triazin-3-yl group can be etherified to a readily hydrolyzable ether, Hal represents bromine or chlorine and the carboxy group can be present in protected form, with thiourea and cleaving off a carboxy protecting group which may be present, (b) for the manufacturing of a readily hydrolyzable ester or ether of a compound of formula I, subjecting a carboxylic acid or an enol of formula I to a corresponding esterification or etherification, or (c) for the manufacturing of salts or hydrates of a compound of formula I or hydrates of said salts, converting a compound of formula I into a salt or hydrate or into a hydrate of said salt.

If desired, the carboxy group present in the starting material of formula II can be protected; for example, by esterification to form a readily cleavable ester such as a silyl ester (e.g. the trimethylsilyl ester). The carboxy group can also be protected in the form of one of the aforementioned readily hydrolyzable esters. Furthermore, the carboxy group can be protected by salt formation with an inorganic or tertiary organic base such as triethylamine.

The starting materials of formula II can be prepared, for example, by N-acylating a corresponding 7-amino compound, namely by converting a compound of the general formula

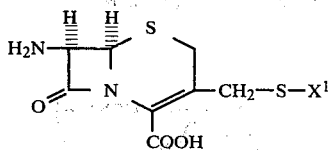

in which $X^1$ is as above and the carboxy group and/or the amino group can be present in protected form, with diketene and the corresponding halogen (bromine or chlorine) into the corresponding 4-haloacetoacetamido derivative of the general formula

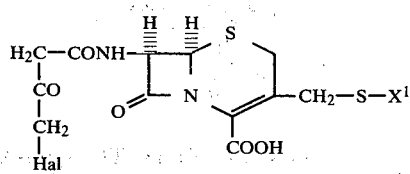

wherein $X^1$ and Hal are as above, and treating this derivative with a nitrosating agent.

If desired, the carboxy group present in the 7-amino compound of formula III can be protected in the same manner as mentioned hereinbefore in connection with the starting material of formula II. The amino group of the compound of formula III can be protected, for example, by a silyl protecting group such as trimethylsilyl.

The reagents diketene or bromine (or chlorine) required for the preparation of the compounds IV from a compound III are preferably used in equimolar amounts. The reaction is carried out as far as practicable in an inert organic solvent (e.g. methylene chloride, chloroform, tetrahydrofuran or mixtures thereof) at a low temperature (e.g. at −5° C. to 0° C.). The subsequent nitrosation of the resulting compound of formula IV can be carried out by treatment with nitrous acid or an ester thereof (e.g. methyl, ethyl or amyl nitrite) or nitrosyl chloride. The nitrosation is preferably carried out in an inert solvent (e.g. water, acetic acid, dioxan, tetrahydrofuran, acetonitrile or mixtures thereof) at a temperature between about −20° C. and 50° C., preferably at room temperature. Under these conditions the starting material of formula II is obtained in the syn-form (Z-form) or in the form of mixtures in which the syn-form predominates.

The reaction of a halide of formula II or a salt thereof with thiourea in accordance with process variant (a) is preferably carried out in an inert solvent such as, for example, a lower alkanol (e.g. ethanol), a lower ketone such as acetone, an ether such as tetrahydrofuran or dioxan, dimethylformamide, dimethylacetamide, water or mixtures thereof. The reaction is generally carried out at a temperature in the range of about 0° C. to 60° C., preferably at room temperature. The free acid of formula II or, if desired, also a salt thereof can be used, whereby the same salts as the salts of the compounds of formula I mentioned above come into consideration.

After carrying out process variant (a), a carboxy protecting group which may be present in the reaction product can be cleaved off where desired. When the protecting group is a silyl group (silyl ester), this group can be cleaved off especially readily by treating the reaction product with water. Lower alkanoyloxyalkyl, alkoxycarbonyloxyalkyl, lactonyl, alkoxymethyl and alkanoylaminomethyl esters are preferably cleaved enzymatically with the aid of a suitable esterase (at about 20°–40° C.). When the carboxy group is protected by salt formation (e.g. with triethylamine), then the cleavage of this salt-forming protecting group is carried out by treatment with acid. The acid which can be used for this purpose can be, for example, hydrochloric acid, sulphuric acid, phosphoric acid or citric acid.

In order to manufacture the readily hydrolyzable esters of the carboxylic acids of formula I in accordance with variant (b), the carboxylic acid is preferably reacted with the corresponding halide, preferably with the iodide, containing the ester group. The reaction can be accelerated with the aid of a base, for example, an alkali metal hydroxide or carbonate or an organic amine such as triethylamine. When the 2,5-dihydro-6-hydroxy-2-methyl-5-oxo-as-triazin-3-yl group X with its enolic function is present, this is etherified with the formation of a corresponding readily hydrolysable ether. In this case an excess of the corresponding halide is preferably used. The esterification/etherification is preferably carried out in an inert organic solvent, such as dimethylacetamide, hexamethylphosphoric acid triamide, dimethyl sulphoxide or, preferably, dimethylformamide. The temperature preferably lies in the range of about 0°–40° C.

The manufacture of the salts and hydrates of the compounds of formula I or the hydrates of these salts can be carried out in a manner known per se; for example, by reacting the carboxylic acid of formula I with an equivalent amount of the desired base, conveniently in a solvent such as water or in an organic solvent such as ethanol, methanol, acetone etc. When a second equivalent of base is used, salt formation also takes place on a tautomeric enol form which may be present (2,5-dihydro-6-hydroxy-2-methyl-5-oxo-as-triazin-3-yl group X), whereby a di-salt results. The temperature at which the salt formation is carried out is not critical. It is generally carried out at room temperature, but it can also be carried out at a temperature slightly above or below room temperature (e.g. in the range of 0° C. to +50° C.).

The manufacture of the hydrates usually takes place automatically in the course of the manufacturing process or as a result of the hygroscopic properties of an initially anhydrous product. For the controlled manufacture of a hydrate, a completely or partially anhydrous product (carboxylic acid of formula I or ester, ether or salt thereof) can be exposed to a moist atmosphere (e.g. at about +10° C. to +40° C.).

The 7-amino compounds of formula III used above can be prepared by reacting a compound of the formula

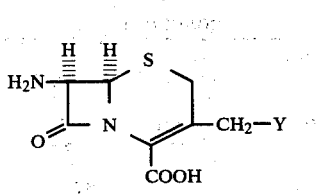

in which Y is a leaving group and the carboxy group can be protected by salt formation with an inorganic or tertiary organic base, with a thiol of the general formula

HS-X¹  VI in which X¹ is as above.

This reaction can be carried out in a manner known per se; for example, at a temperature between about 40° and 80° C., conveniently at about 60° C., in water or in a buffer solution with a pH of about 6 to 7, preferably 6.5.

The carboxy group and/or the amino group of the resulting compound of formula III can be protected if desired; for example, by esterification or salt formation at the carboxy group or by silylation.

The thiols of formula VI are in tautomeric equilibrium with the corresponding thiones as shown in the following formulae

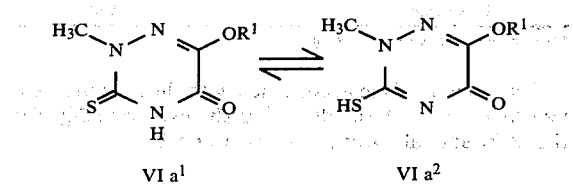

wherein R¹ represents hydrogen or (together with the oxygen) a readily hydrolyzable ether group.

When R¹ represents hydrogen in formulae VI a¹ and VI a², these 6-hydroxy compounds are in tautomeric equilibrium with the corresponding 6-oxo compounds as shown in the following formulae:

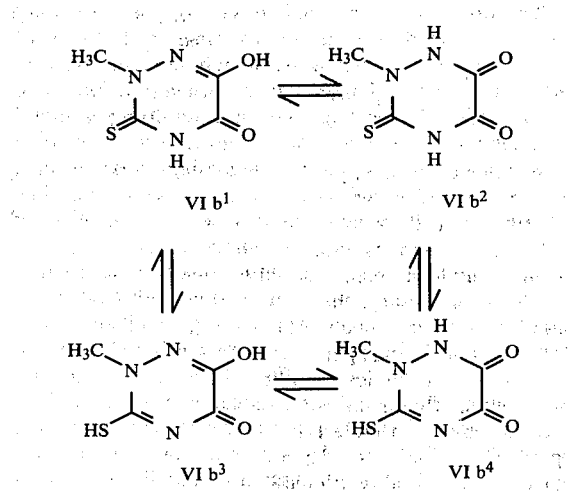

The preparation of thiols (thiones) of formula VI which are etherified in the 6-position is described in Example 2. The ether group is generally introduced by reacting a S-protected thiol (e.g. by benzhydryl) with the halide containing the ether group, preferably the iodide, in an inert organic solvent in the presence of an acid-binding agent (e.g. potassium carbonate), preferably at about 10°–50° C., and cleaving off the protecting group (benzhydryl can be cleaved off with anisole and trifluoroacetic acid at room temperature).

A syn/anti mixture of a compound of formula I which may be obtained can be separated into the corresponding syn- and anti-forms in the usual manner, for example by recrystallization or by chromatographical methods using a suitable solvent or solvent mixture.

The compounds of formula I as well as the corresponding readily hydrolyzable esters, readily hydrolyzable ethers and salts and the hydrates of same have anti-biotic, especially bactericidal, activity. They possess a broad spectrum of activity against gram-positive and gram-negative microorganisms, including β-lactamase-forming Staphylococci and various β-lactamase-forming gram-negative bacteria such as, for example Pseudomonas aeruginosa, Haemophilus influenzae, Escherichia coli, Serratia marcescens and Proteus, Neisseria and Klebsiella species. A particular characteristic is the surprisingly high half-life of the products in vivo (time taken for the active substance titre in the blood plasma to decrease to half), which brings with it the important advantage that, irrespective of differences in the specific bactericidal activity in comparison with other products having low half-lives, a smaller amount of active substance is required for the control of a corresponding infection; further, longer intervals between administrations can be allowed to maintain a desired minimum titre of active substance in the blood.

The compounds of formula I as well as the corresponding readily hydrolyzable esters, readily hydrolyzable ethers and salts and the hydrates of same can be used for the treatment and prophylaxis of infectious diseases. A daily dosage of about 0.1 g to about 2 g is envisaged for adults. The parenteral administration of the compounds in accordance with the invention is especially preferred.

In order to demonstrate the antimicrobial activity of the products in accordance with the invention, the following representative members were tested against various pathogens. The following products were tested:

Product A: (6R,7R)-7-[2-(2-Amino-4-thiazolyl)-2-(Z-hydroxyimino)acetamido]-3-/[(2,5-dihydro-6-hydroxy-2-methyl-5-oxo-as-triazin-3-yl)-thio]methyl/-8-oxo-5-thia-1-azabicyclo-[4.2.0]oct-2-ene-2-carboxylic acid disodium salt.

Product B: (6R,7R)-7-[2-(2-Amino-4-thiazolyl)-2-(Z-hydroxyimino)acetamido]-3-[[[2,5-dihydro-2-methyl-5-oxo-6-[(pivaloyloxy)methoxy]-as-triazin-3-yl]thio]methyl]-8-oxo-5-thia-1-azabicyclo[4.2.0]oct-2-ene-2-carboxylic acid sodium salt.

Product C: Methylene-(6R,7R)-7-[2-(2-amino-4-thiazolyl)-2-(Z-hydroxyimino)acetamido]-3-[[[2,5-dihydro-2-methyl-5-oxo-6-[(pivaloyloxy)methoxy]-as-triazin-3-yl]thio]methyl]-8-oxo-5-thia-1-azabicyclo[4.2.0]-oct-2-ene-2-carboxylate pivalate.

The following results relate to the minimum inhibitory concentration (MIC) in vitro (μg/ml):

| Product A/Test in vitro | | MIC (μg/ml) |
|---|---|---|
| Staphylococcus aureus | strain 1 | 0.62 |
| | strain 2: | 1.2 |
| | β-lactamase producing | |
| Escherichia coli | strain 1 | 1.2 |
| | strain 2 | 1.2 |
| | strain 3 | 2.5 |
| | strain 4 | 0.31 |

| | -continued | |
|---|---|---|
| Klebsiella pneumoniae | strain 1 | 0.02 |
| Serratia marcescens | strain 1 | 0.16 |
| | strain 2 | 0.31 |
| | strain 3 | 0.31 |
| | strain 4 | 0.63 |
| | strain 5 | 0.31 |
| | strain 6 | 0.31 |
| | strain 7 | 0.31 |
| | strain 8 | 0.31 |
| | strain 9 | 0.16 |
| Enterobacter cloacae | strain 1 | 20 |
| | strain 2 | >80 |
| Citrobacter freundii | strain 1 | 80 |
| Proteus vulgaris | strain 1 | 0.31 |
| | strain 2 | 0.31 |
| | strain 3 | 0.63 |
| Proteus morganii | strain 1 | ≦0.04 |
| Proteus rettgeri | strain 1 | 0.63 |
| Proteus inconstans | strain 1 | 0.08 |
| Proteus mirabilis | strain 1 | 0.02 |
| Pseudomonas aeruginosa | strain 1 | >80 |
| | strain 2 | >80 |
| | strain 3 | 40 |
| | strain 4 | 80 |
| | strain 5 | >80 |
| | strain 6 | 10 |
| | strain 7 | 5 |
| | strain 8 | 20 |
| | strain 9 | >80 |
| | strain 10 | 10 |
| | strain 11 | 5 |
| | strain 12 | >80 |
| | strain 13 | 80 |
| | strain 14 | >80 |
| | strain 15 | 80 |
| | strain 16 | >80 |
| | strain 17 | >80 |
| Neisseria meningitidis | strain 1 | 0.0025 |
| | strain 2 | 0.0025 |
| | strain 3 | 0.0025 |
| | strain 4 | 0.0012 |
| Neisseria gonorrhoeae | strain 1 | 0.0012 |
| | strain 2 | 0.0012 |
| | strain 3 | 0.02 |
| | strain 4 | 0.01 |
| | strain 5 | 0.04 |
| | strain 6 | 0.0006 |
| Haemophilus influenzae | strain 1 | 0.63 |
| | strain 2 | 0.04 |
| | strain 3 | 0.04 |
| | strain 4 | 0.04 |
| | strain 5 | 0.04 |
| | strain 6 | 0.02 |
| | strain 7 | 0.04 |

| | | MIC (μg/ml) | |
|---|---|---|---|
| Products A and B/Test in vitro | | A | B |
| Staphylococcus aureus | strain 3 | 1.6 | 0.4 |
| | strain 4 | 1.6 | 0.8 |
| | strain 5 | 1.6 | 0.4 |
| | strain 6 | 3.1 | 0.8 |
| Staphylococcus epidermidis | | 1.6 | 0.4 |
| Streptococcus faecalis | strain 1 | 25 | 6.3 |
| | strain 2 | >25 | >25 |
| Streptococcus pyogenes | strain 1 | 0.1 | 0.025 |
| | strain 2 | 0.05 | 0.025 |
| Streptococcus pneumoniae | | 0.4 | 0.1 |
| Streptococcus viridans | | 1.6 | 0.4 |
| Escherichia coli | strain 5 | 0.4 | 0.4 |
| | strain 6 | 0.2 | 0.2 |
| | strain 7 | 0.025 | 0.05 |
| | strain 8 | 0.05 | 0.8 |
| Proteus mirabilis | strain 2 | 0.025 | 0.4 |
| | strain 3 | 0.05 | 1.6 |
| | strain 4 | 0.025 | 0.8 |
| Proteus inconstans | strain 2 | 0.01 | 0.2 |
| | strain 3 | ≦0.025 | ≦0.025 |
| Proteus vulgaris | strain 4 | 3.1 | 12.5 |
| | strain 5 | 0.1 | 0.8 |
| | strain 6 | 0.05 | 0.8 |
| Proteus morganii | strain 2 | 0.05 | 1.6 |
| Proteus rettgeri | strain 2 | 0.05 | 0.4 |
| Klebsiella pneumoniae | strain 2 | 0.1 | 1.6 |
| | strain 3 | 0.025 | 0.4 |
| | strain 4 | 0.05 | 0.8 |
| Serratia marcescens | strain 10 | 0.8 | 6.3 |
| | strain 11 | 6.3 | 12.5 |
| | strain 12 | 0.1 | 1.6 |
| Enterobacter cloacae | strain 3 | >25 | >25 |
| | strain 4 | 12.5 | 6.3 |
| Enterobacter aerogenes | strain 1 | 0.1 | 0.2 |
| | strain 2 | 0.8 | 1.6 |
| Citrobacter freundii | strain 2 | 6.3 | 3.1 |
| | strain 3 | 0.2 | 0.4 |

In order to demonstrate the high half-life of the products in accordance with the invention 20 mg of product A were administered i.v. to rats. A half-life of 140 minutes was established.

The long retention of the products in accordance with the invention in the organism is also evident after the s.c. treatment of mice with product A or C 5 hours before a i.p. infection with the microorganism to be tested, the following $ED_{50}$ values being ascertained:

| | $ED_{50}$ mg/kg s.c. | |
|---|---|---|
| Pathogen | A | C |
| Streptococcus pyogenes | 0.15 | 0.45 |
| Serratia marcescens | 0.89 | |
| Escherichia coli | | 5.6* |

*Administered 24 hours before the infection.

The compounds in accordance with the invention are non-toxic, as will be evident from the following data for the 24 hours values of products A and B:

| | Lethal dosage mg/kg | Tolerated dosage mg/kg | |
|---|---|---|---|
| Route of administration | A | A | B |
| Oral | >5000 | 5000 | >5000 |
| Subcutaneous | >4000 | | >4000 |
| Intravenous | 1000 | 500 | |

The products in accordance with the invention can be used as medicaments, for example in the form of pharmaceutical preparations which contain them in admixture with a pharmaceutical, organic or inorganic inert carrier material suitable for enteral or parenteral administration such as, for example, water, gelatine, gum arabic, lactose, starch, magnesium stearate, talc, vegetable oils, polyalkyleneglycols, Vaseline etc. The pharmaceutical preparations can be made up in solid form (e.g. as tablets, dragees, suppositories or capsules) or in liquid form (e.g., as solutions, suspensions or emulsions). If necessary, they can be sterilized and/or can contain adjuvants such as preserving, stabilizing, wetting or emulsifying agents, salts for varying the osmotic pressure, anaesthetics or buffers. They can also contain still other therapeutically valuable substances. The compounds of formula I and their salts or hydrates are preferably administered parenterally and for this purpose are preferably prepared as lyophilizates or dry powders for dilution with usual agents such as water or isotonic sodium chloride solution. The readily hydrolyzable esters or readily hydrolyzable ethers of the compounds of formula I and their salts or hydrates are also suitable for enteral (e.g. oral) administration.

The following Examples illustrate the present invention:

EXAMPLE 1

Manufacture of the disodium salt of (6R,7R)--7-[2-(2-amino-4-thiazolyl)-2-(Z-hydroxyimino)acetamido]-3-/[(2,5-dihydro-6-hydroxy-2-methyl-5-oxo-as-triazin-3-yl)thio]methyl/-8-oxo-5-thia-1-azabicyclo[4.2.0]oct-2-ene-2-carboxylic acid:

10 g of (6R,7R)-7-[4-bromo-2-(Z-hydroxyimino)-acetoacetamido]-8-oxo-3-/[(1,2,5,6-tetrahydro-2-methyl-5,6-dioxo-as-triazin-3-yl)thio]methyl/-5-thia-1-azabicyclo[4.2.0]oct-2-ene-2-carboxylic acid are dissolved in 50 ml of acetone and added to a solution of 3.5 g of thiourea in 150 ml of acetone. The hydrobromide, which precipitates immediately, is filtered off under suction and washed with acetone and low-boiling petroleum ether. Pink hydrobromide is obtained as the crude product. For the conversion into the disodium salt, the crude product is dissolved in a mixture of 100 ml of water and 100 ml of methanol and treated with 40 ml of a 2N solution of sodium 2-ethylcaproate in ethyl acetate. Active carbon is added to the orange coloured solution, the mixture is stirred for 1 hour at 25° C., then filtered and the filtrate is diluted with methanol to a volume of 2 l. A small amount of precipitated material (Fraction 1, brown) is filtered off. The filtrate is concentrated in vacuo at 40° C. to about 800 ml and precipitated substance (Fraction 2, yellow) is filtered off. The filtrate is concentrated to about 200 ml and diluted with 1 l of methanol, whereupon the pecipitated substance is filtered off (Fraction 3, yellow). The filtrate is concentrated in vacuo at 40° C. to a volume of about 300 ml and precipitated substance is filtered off (Fraction 4, yellow). The filtrate is treated with 1 l of ethanol and the material which precipitates in amorphous form is filtered off (Fraction 5, beige). According to thin-layer chromatographic and nuclear resonance analysis, Fractions 2,3 and 4 are identical and are the desired compound; Fractions 1 and 5 are, on the other hand, mixtures and are discarded. After drying Fractions 2, 3 and 4 in a high vacuum at 40° C. overnight, there is obtained yellow, amorphous title compound with $[\alpha]_D^{25} = -133.2°$ (c=1 in water). The substance contains 4% water and 3% methanol.

The (6R,7R)-7-[4-bromo-2-(Z-hydroxyimino)-acetoacetamido]-8-oxo-3-/[(1,2,5,6-tetrahydro-2-methyl-5,6-dioxo-as-triazin-3-yl)thio]methyl/-5-thia-1-azabicyclo[4.2.0]oct-2-ene-carboxylic acid used as the starting material in the above process can be prepared as follows:

5.44 g of diketene are dissolved in 25 ml of dichloromethane and treated dropwise during about 15 minutes at −30° to −40° C. with a solution of 10.4 g of bromine in 25 ml of dichloromethane. The colourless solution is cooled to −50° C. and added dropwise during about 10 minutes at −20° C. to a solution prepared by treating 18.5 g of (7R)-7-amino-3-desacetoxy-3[(2,5-dihydro-6-hydroxy-2-methyl-5-oxo-as-triazin-3-yl)thio]-cephalosporanic acid in 300 ml of absolute tetrahydrofuran with 50 ml of N,O-bis-(trimethylsilyl)-acetamide during 30 minutes. The mixture is stirred for 30 minutes without cooling, the temperature rising to 0° C. The orange-brown mixture is then poured into 2 l of ethyl acetate and vigorously stirred with 500 ml of water. The thus-formed intermediate layer is filtered off and discarded. The orange coloured organic phase is washed three times with 500 ml of water each time and subsequently, without being dried, stirred with 10 g of active carbon for 1½ hours. After filtration of the carbon, the light yellow filtrate is dried over sodium sulphate and concentrated to a volume of about 100 ml in vacuo at 40° C. The substance which thereby crystallizes out is filtered off under suction and washed with a small amount of ethyl acetate. There is obtained pure beige coloured (6R,7R)-7-(4-bromoacetoacetamido)-8-oxo-3-/[(1,2,5,6-tetrahydro-2-methyl-5,6-dioxo-as-triazin-3-yl)thio]methyl/-5-thia-1-azabicyclo[4.2.0]oct-2-ene-2-carboxylic acid. Additional colourless, amorphous pure substance is obtained from the mother liquor by precipitation with ether. $[\alpha]_D^{20} = -247.3°$ (c=1 in dimethylformamide).

46.4 g of (6R,7R)-7-(4-bromoacetoacetamido)-8-oxo-3-/[(1,2,5,6-tetrahydro-2-methyl-5,6-dioxo-as-triazin-3-yl)thio]methyl/-5-thia-1-azabicyclo[4.2.0]oct-2-ene-2-carboxylic acid are suspended in 100 ml of glacial acetic acid and treated at 10°-15° C. with a solution of 2.5 g of sodium nitrite in 10 ml of water during about 15 minutes. The mixture is stirred for 1½ hours at 10° C. The thus-obtained, orange coloured solution is poured into 1 l of ethyl acetate, washed once with 600 ml of 0.16 N sulphuric acid and then three times with 500 ml of water each time, dried over sodium sulphate and concentrated strongly in vacuo at 40° C. The concentrate is treated with ether, the substance precipitating in amorphous form. This substance is filtered off under suction, washed successively with ether and low-boiling petroleum ether and dried in vacuo at 25° C. There is obtained beige coloured (6R,7R)-7-[4-bromo-2-(Z-hydroxyimino)acetoacetamido]-8-oxo-3-/[(1,2,5,6-tetrahydro-2-methyl-5,6-dioxo-as-triazin-3-yl)thio]methyl/-5-thia-1-azabicyclo[4.2.0]oct-2-ene-2-carboxylic acid with $[\alpha]_D^{20} = -279.2°$ (c=1 in dimethylformamide).

EXAMPLE 2

Manufacture of the sodium salt of (6R,7R)-7-[2-(2-amino-4-thiazolyl)-2-(Z-hydroxyimino)acetamido]-3-[[[2,5-dihydro-2-methyl-5-oxo-6-[(pivaloyloxy)methoxy]-as-triazin-3-yl]thio]methyl]-8-oxo-5-thia-1-azabicyclo[4.2.0]oct-2-ene-2-carboxylic acid:

5.4 g of (6R,7R)-7-[4-bromo-2-(Z-hydroxyimino)-acetoacetamido]-3-[[[2,5-dihydro-2-methyl-5-oxo-6-[(pivaloyloxy)methoxy]-as-triazin-3-yl]thio]methyl]-8-oxo-5-thia-1-azabicyclo[4.2.0]oct-2-ene-2-carboxylic acid are suspended in 70 ml of ethanol and treated with 1.2 g of thiourea. The resulting yellow solution is stirred for 25 minutes at 25° C. Then, 9 ml of a 2N solution of sodium 2-ethylcaproate in ethyl acetate are added thereto, the substance precipitating in very fine form. After adding 300 ml of methanol and 130 ml of ethanol, the slightly turbid solution is filtered and the light yellow filtrate is concentrated to a volume of about 100 ml in vacuo at 40°. The material which thereby precipitates is filtered off under suction, washed with ethanol and low-boiling petroleum ether and dried overnight in a high vacuum at 40° C. There is obtained pure, beige coloured, amorphous title compound with $[\alpha]_D^{25} = -133.3°$ (c=1 in water). The nuclear resonance spectrum and the microanalysis correspond to the given structure.

The (6R,7R)-7-[4-bromo-2-(Z-hydroxyimino)-acetoacetamido]-3-[[[2,5-dihydro-2-methyl-5-oxo-6-[(pivaloyloxy)methoxy]-as-triazin-3-yl]thio]methyl]-8-oxo-5-thia-1-azabicyclo[4.2.0]oct-2-ene-2-carboxylic acid used as the starting material in the above process can be prepared as follows:

(a) Preparation of tetrahydro-2-methyl-5,6-dioxo-3-thioxo-as-triazine-1(2H)-carboxylic acid benzyl ester:

39.79 g of 1,2,5,6-tetrahydro-5,6-dioxo-3-mercapto-2-methyl-as-triazine are dissolved in 500 ml of dimethylformamide and treated with 35 ml of triethylamine. 39 ml of benzyloxycarbonyl chloride are added dropwise during 15 minutes, the temperature of the mixture rising to 45° C., triethylamine hydrochloride precipitating and the suspension becoming yellow coloured. The mixture is stirred for 2½ hours ar 25° C. and subsequently evaporated in vacuo at 70° C. The oily evaporation residue is stirred with 500 ml of water for 1 hour, whereby it becomes solid. The solid obtained is filtered off under suction and washed with 50 ml of water. The yellow filter material is stirred well with 250 ml of ethanol, filtered off under suction, washed with ethanol and dried in vacuo at 40° C. There is obtained colourless crude crystallizate which is recrystallized from methanol and yields colourless pure substances of m.p. 150°–153° C.

(b) Preparation of 3-[(diphenylmethyl)thio]-5,6-dihydro-2-methyl-5,6-dioxo-as-triazine-1(2H)-carboxylic acid benzyl ester:

13.2 g of tetrahydro-2-methyl-5,6-dioxo-3-thioxo-as-triazine-1(2H)-carboxylic acid benzyl ester are dissolved in 500 ml of ethyl acetate and treated with a solution of diphenyldiazomethane in 90 ml of low-boiling petroleum ether. The initially violet solution is left to stand for 40 hours at 25° C., the colour becoming pink. 3 ml of galcial acetic acid are added and, after 1 hour, the mixture is evaporated in vacuo at 40° C. A yellow oil is obtained as the evaporation residue. This is separated by column chromatography on silica gel using benzene, benzene/ethyl acetate (95:5) and benzene/ethyl acetate (90:10) for the elution. The fractions containing the desired substance are combined and evaporated in vacuo at 40° C. After recrystallization from ethanol, there is obtained colourless pure substance of m.p. 90°–92° C.

(c) Preparation of 3-[(diphenylmethyl)thio]-1,2-dihydro-2-methyl-as-triazine-5,6-dione:

6.9 g of the substance prepared under (b) are dissolved in 100 ml of ethyl acetate and stirred well with 30 ml of an aqueous, 7% ammonia solution at 25° C. for 15 minutes. The ethyl acetate phase is separated and discarded. The aqueous phase is treated with 7 ml of concentrated hydrochloric acid and stirred for 30 minutes in an ice-bath. The substance which thereby precipitates is filtered off under suction, washed with water and immediately recrystallized from ethanol. There is obtained colourless pure substance of m.p. 180°–182° C.

(d) Preparation of 3-[(diphenylmethyl)thio]-6-pivaloyloxymethoxy-2-methyl-as-triazine-6(2H)-one:

3.25 g of the compound prepared under (c) are dissolved in 40 ml of dimethylformamide and treated with 1.52 g of potassium carbonate. 2.66 g of pivaloyloxymethyl iodide are added in one portion to this mixture, a pale yellow solution resulting. The mixture is stirred for 4 hours at 25° C. and treated once more with 2.66 g of pivaloyloxymethyl iodide. The mixture obtained is stirred for 15 hours at 25° C. and subsequently evaporated in a high vacuum at 35° C. The resulting evaporation residue is partitioned between 100 ml of water and 100 ml of ethyl acetate. The aqueous phase is extracted twice more with 50 ml of ethyl acetate each time. The combined ethyl acetate phases are dried over sodium sulphate and evaporated in vacuo at 35° C. The residual yellow oil is chromatographed on a silica gel column using ethyl acetate for the elution agent. The fractions containing the desired product are combined and evaporated in vacuo at 35° C. The residual pale blue oil is dried in a high vacuum at 25° C. for 1 hour, the pure substance being obtained as a pale blue resin.

(e) Preparation of [(2,3,4,5-tetrahydro-2-methyl-5-oxo-3-thioxo-as-triazin-6-yl)oxy]methyl pivalate:

3.6 g of the compound prepared under (d) are stirred in 18 ml of anisole and 18 ml of trifluoroacetic acid for 2½ hours at 25° C. The solution is then evaporated in vacuo at 50° C. The oily residue is stirred up with 50 ml of low-boiling petroleum ether, crystallization occurring. The crystallizate is filtered off under suction and washed with low-boiling petroleum ether. There are obtained white crystals which, after recrystallization from ether/low-boiling petroleum ether, yield white, crystalline pure substance of m.p. 112°–113° C. The nuclear resonance spectrum and the microanalysis correspond to the given structure.

(f) Preparation of (6R,7R)-7-amino-3-[[[2,5-dihydro-2-methyl-5-oxo-6-[(pivaloyloxy)methoxy]-as-triazin-3-yl]thio]methyl]-8-oxo-5-thia-1-azabicyclo[4.2.0]oct-2-ene-2-carboxylic acid:

3.0 g of the compound prepared under (e) are suspended together with 2.72 g of 7-aminocephalosporanic acid in 50 ml of water. The suspension is adjusted to pH 6.5 with 1N sodium hydroxide while gassing with nitrogen and stirred for 4 hours at pH 6.5–7 and 55°–60° C. The desired compound precipitates out and, after cooling the mixture to 25° C., is filtered off under suction. After washing with water, acetone and low-boiling petroleum ether and drying overnight in a high vacuum at 40° C., there is obtained the pure substance, the microanalysis and nuclear resonance spectrum of which correspond to the given structure.

(g) Preparation of (6R,7R)-7-[4-bromo-acetoacetamido]-3-[[[2,5-dihydro-2-methyl-5-oxo-6-[(pivaloyloxy)-methoxy]-as-triazin-3-yl]thio]methyl]-8-oxo-5-thia-1-azabicyclo[4.2.0]oct-2-ene-2-carboxylic acid:

Firstly, 4.35 g of diketene are dissolved in 20 ml of methylene chloride and treated dropwise during about 15 minutes at −30° to −40° C. with a solution of 8.32 g of bromine in 20 ml of methylene chloride. The colourless solution containing the acid bromide is cooled to −50° C. and added dropwise during about 10 minutes at −20° C. to a solution prepared as follows: 19.42 g of the compound prepared under (f) are suspended in 400 ml of ethyl acetate and treated with 40 ml of N,O-bis-(trimethylsilyl)acetamide. The suspension is stirred at 35°–40° C. for 30 minutes until a brownish solution has resulted. For the acylation with the acid bromide prepared as described above, this solution is cooled to −20° C. After the dropwise addition of the acid bromide solution, the mixture is stirred for a further 1 hour without cooling. Thereafter, 200 ml of water are added. The precipitated, unreacted starting material is filtered off under suction and discarded. The aqueous is separated. The orange coloured orange phase is washed twice with 250 ml of water each time, dried over sodium sulphate and concentrated in vacuo at 40° C. The product precipitates in amorphous form after adding ether. The product is filtered off under suction, washed with ether and low-boiling petroleum ether and dried in vacuo at 25° C. there is obtained crude amorphous substance which, for purification, is reprecipitated from ethyl acetate/ether. There is thus obtained the beige coloured title compound with $[\alpha]_D^{25} = -159.3°$ (c=1 in chloroform).

(h) Preparation of (6R,7R)-7-[4-bromo-2-(Z-hydroxyimino)acetoacetamido]-3-[[[2,5-dihydro-2-methyl-5- xo-6-[(pivaloyloxy)methoxy]-as-triazin-3-yl]thio]methyl]-8-oxo-5-thia-1-azabicyclo[4.2.0]oct-2-ene-2-carboxylic acid:

13 g of the compound prepared under (g) are dissolved in 65 ml of acetic acid. This solution is treated dropwise at 10°–15° C. during about 45 minutes with a solution of 1.65 g of sodium nitrite in 7 ml of water. The solution is stirred for a further 1¼ hours at 10°–15° until nitrous acid can no longer be detected by means of potassium iodide/starch paper. The reddish solution is then poured into 500 ml of ethyl acetate. This mixture is washed twice with dilute sodium chloride solution. The organic phase is dried with sodium sulphate and concentrated strongly in vacuo at 40° C. The residual syrupy residue is treated with ether, the substance precipitating in amorphous form. Thus substance is filtered off under suction, washed with ether and with low-boiling petroleum ether and dried overnight in vacuo at 40° C. There is obtained a brownish, amorphous powder which, for purification, is stirred up in 100 ml of isopropanol, there firstly resulting a solution from which there separates a gelatinous mass which crystallizes after stirring for about 45 minutes at 25° C. The crystalline substance is filtered off under suction, washed with a small amount of isopropanol, ether and low-boiling petroleum ether and dried in a high vacuum at 40° C. There is obtained the white, crystalline pure substance with $[\alpha]_D^{25} = -284.6°$ (c=1 in chloroform). The nuclear resonance spectrum corresponds to the given structure.

EXAMPLE 3

Manufacture of methylene-(6R,7R)-7-[2-(2-amino-4-thiazolyl)-2-(Z-hydroxyimino)acetamido]-3-[[[2,5-dihydro-2-methyl-5-oxo-6[(pivaloyloxy)methoxy]-as-triazin-3-yl]thio]methyl]-8-oxo-5-thia-1-azabicyclo[4.2.-0]oct-2-ene-2-carboxylate pivalate:

1.35 g of the sodium salt of (6R,7R)-7-[2-(2-amino-4-thiazolyl)-2-(Z-hydroxyimino)acetamido]-3-[[[2,5-dihydro-2-methyl-5-oxo-6-[(pivaloyloxy)methoxy]-as-triazin-3-yl]thio]methyl]-5-oxo-4-thia-1-azabicyclo[4.2.-0]oct-2-ene-2-carboxylic acid are dissolved in 25 ml of dimethylformamide and treated at 0.5° C. with 1 g of pivaloyloxymethyl iodide. The mixture is stirred for 30 minutes at 0°–5° while gassing with nitrogen. Thereafter, the mixture is poured into 400 ml of ethyl acetate, washed successively twice with 100 ml of water each time, twice with 50 ml of 8% sodium hydrogen carbonate solution each time, once with 100 ml of 5% sodium thiosulphate solution and twice with 100 ml of water each time and finally dried over sodium sulphate. The ethyl acetate solution is then concentrated in vacuo at 40° C. and treated with 150 ml of ether, the substance precipitating in amorphous form. This substance is filtered off under suction, washed with ether and low-boiling petroleum ether and dried overnight in a high vacuum at 40°–45° C. There is obtained beige coloured pure substance with $R_f=0.57$ in the tlc system butanol-/acetic acid/water (4:1:1) on Kieselgel-$F_{254}$ plates. The nuclear resonance spectrum corresponds to the given structure.

EXAMPLE 4

Manufacture of dry ampoules for intramuscular administration:

A lyophilizate of 1 g of the disodium salt of (6R,7R)--7-[2-(2-amino-4-thiazolyl)-2-(Z-hydroxyimino)acetamido]-3-/[(2,5-dihydro-6-hydroxy-2-methyl-5-oxo-as-triazin-3-yl)thio]methyl/-8-oxo-5-thia-1-azabicyclo[4.2.0]oct-2-ene-2-carboxylic acid is prepared in the usual manner and filled into an ampoule. Prior to the administration, the lyophilizate is treated with 2.5 ml of a 2% aqueous lidocaine hydrochloride solution.

EXAMPLE 5

An interlocking gelatine capsule containing the following ingredients is prepared in the usual manner:

| | |
|---|---|
| Methylene-(6R,7R)-7-[2-(2-Amino-4-thiazolyl)-2-(Z-hydroxyimino)acetamido]-3-[[[2,5-dihydro-2-methyl-5-oxo-6-[(pivaloyloxy)methoxy]-as-triazin-3-yl]thio]methyl]-8-oxo-5-thia-1-azabicyclo[4.2.0]oct-2-ene-2-carboxylat pivalate | 500 mg |
| Luviskol (water-soluble polyvinylpyrrolidone) | 20 mg |
| Mannitol | 20 mg |
| Talc | 15 mg |
| Magnesium stearate | 2 mg |
| | 557 mg |

What is claimed:
1. A compound of the formula

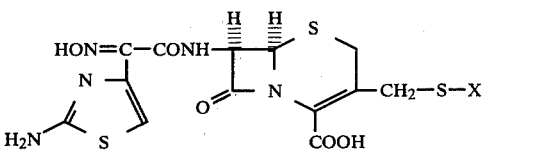

wherein X is the 1,2,5,6-tetrahydro-2-methyl-5,6-dioxo-as-triazin-3-yl group or its corresponding tautomeric form, the 2,5-dihydro-6-hydroxy-2-methyl-5-oxo-as-triazin-3-yl group, and the readily hydrolyzable esters, readily hydrolyzable ethers and salts thereof and hydrates of the compound of formula I or the esters, ethers and salts thereof.

2. The compound of claim 1 wherein the compound is in the syn-isomeric form or in a mixture in which the syn-isomer form predominates.

3. The compound: (6R,7R)-7-[2-(2-Amino-4-thiazolyl)-2-(Z-hydroxyimino)-acetamido]-3-/[2,5-dihydro-6-hydroxy-2-methyl-5-oxo-as-triazin-3-yl)thio]-methyl/-8-oxo-5-thia-1-azabicyclo[4.2.0]oct-2-ene-2-carboxylic acid and the salts and hydrates thereof or salts of said hydrates.

4. The compound of claim 1 wherein said compound is in the form of a readily hydrolyzable ether.

5. The compound of claim 4 wherein the compound is a pivaloyloxymethyl ether and the salts thereof and hydrates of said ether or salts thereof.

6. The compound: (6R,7R)-7-[2-(2-Amino-4-thiazolyl)-2-(Z-hydroxyimino)acetamido]-3-[[[2,5-dihydro-2-methyl-5-oxo-6-[(pivaloyloxy)methoxy]-as-triazin-3-yl]-thio]methyl]-8-oxo-5-thia-1-azabicyclo[4.2.0]oct-2-2-ene-2-carboxylic acid and the salts thereof and hydrates of the ether and its salts.

7. The compound of claim 1 wherein said compound is in the form of a pivaloyloxymethyl ester.

8. The compound: methylene-(6R,7R-7-[2-(2-amino-4-thiazolyl)-2-(Z-hydroxyimino)-acetamido]-3-[[[2,5-dihydro-2-methyl-5-oxo-6-[(pivaloyloxy)methoxy]-as-triazin-3-yl]thio]methyl]-8-oxo-5-thia-1-azabicyclo[4.2.0]oct-2-ene-2-carboxylate pivalate and the salts thereof and hydrates of the compound and its salts.

* * * * *